US008083998B2

(12) United States Patent
Hurwitz et al.

(10) Patent No.: US 8,083,998 B2
(45) Date of Patent: Dec. 27, 2011

(54) STERILIZING DEVICE FOR MEDICAL INSTRUMENTS

(75) Inventors: Joshua Hurwitz, Albany, NY (US); Charles Edward Nokes, Jr., Vancouver, WA (US)

(73) Assignee: Redpoint International, Inc., Vancouver, WA (US)

( * ) Notice: Subject to any disclaimer, the term of this patent is extended or adjusted under 35 U.S.C. 154(b) by 377 days.

(21) Appl. No.: 12/408,526

(22) Filed: Mar. 20, 2009

(65) Prior Publication Data
US 2009/0238738 A1 Sep. 24, 2009

Related U.S. Application Data

(60) Provisional application No. 61/070,411, filed on Mar. 20, 2008.

(51) Int. Cl.
*A61L 2/00* (2006.01)
(52) U.S. Cl. ...................................................... 422/292
(58) Field of Classification Search .................. 422/292
See application file for complete search history.

(56) References Cited

U.S. PATENT DOCUMENTS

| 5,466,898 | A | 11/1995 | Gilbert et al. | |
|---|---|---|---|---|
| 5,892,233 | A | 4/1999 | Clement | |
| 6,018,835 | A | 2/2000 | Schonfeld | |
| 6,186,957 | B1 | 2/2001 | Milam | |
| 7,406,973 | B1 * | 8/2008 | Perlman et al. | ........... 134/166 R |

FOREIGN PATENT DOCUMENTS
WO WO 02/094326 A1 11/2002

OTHER PUBLICATIONS

Marinella. M. A., Pierson, C., Chenoweth, C., "The stethoscope. A potential source of nosocomial infection?," Archives of Internal Medicine. Apr. 14, 1997, 5 pages.
Wenzel, Richard P., Edmond, Michael B., "The Impact of Hospital-Acquired Bloodstream Infections," Emerging Infectious Diseases. Mar.-Apr. 2001, pp. 174-177. Medical College of Virginia, Richmond, Virginia, USA.
"The war against super bugs," CBC News in Depth: Hospital infections, May 31, 2007, 3 pages, CBC News, Canada.
Sack, Kevin, "Swabs in Hand, Hospital Cuts Deadly Infections," The New York Times, Jul. 27, 2007, 4 pages, New York Times, USA.
Marlantes, Liz. "Medicare Won't Cover Hospital Mistakes" ABC News, Aug. 19, 2007, 2 pages, ABC News, USA.
"Medicare Ends Reimbursement for Some Hospital-acquired Conditions," IDSA News, Sep. 2007, 3 pages, Arlington, VA, USA.
Appleby, Julie, "Hospital-acquired infections take toll on bottom lines," USA Today, Nov. 21, 2006, 2 pages. USA.

* cited by examiner

*Primary Examiner* — Kevin Joyner
(74) *Attorney, Agent, or Firm* — Law Office of Karen Dana Oster, LLC.

(57) ABSTRACT

A sterilizing device for sterilizing at least a portion of a medical instrument including a housing, a reservoir suitable for containing sterilizing agent, a delivery system for conducting the sterilizing agent from the reservoir to a permeable membrane, and a lock out system that blocks access to the permeable membrane when insufficient sterilizing agent is present in the reservoir. In preferred embodiments the delivery mechanism is activatable by pressure applied to the permeable membrane by the at least a portion of the medical instrument (e.g. a head of a stethoscope).

11 Claims, 1 Drawing Sheet

STERILIZING DEVICE FOR MEDICAL INSTRUMENTS

The present application is an application claiming the benefit under 35 USC Section 119(e) of U.S. Provisional Patent Application Ser. No. 61/070,411, filed Mar. 20, 2008. The present application is based on and claims priority from this application, the disclosure of which is hereby expressly incorporated herein by reference in its entirety.

BACKGROUND OF INVENTION

The present invention relates generally to devices for cleaning, disinfecting, and/or sterilizing a medical instrument in a rapid convenient manner. In a specific embodiment, the invention relates to a sterilizing device for instantaneously disinfecting a stethoscope.

Hospital-acquired infections, or "nosocomial" infections, are a common cause of mortality and morbidity in the hospital setting. Indeed, nosocomial infections are estimated to occur in 5% of all acute-care hospitalizations and upwards of 90,000 deaths each year can be attributed to hospital-acquired infections in the US alone.

Methicillin-resistant *Staphylococcus aureus* (MRSA) is a type of bacteria that is resistant to certain antibiotics. These antibiotics include methicillin and other more common antibiotics such as oxacillin, penicillin, and amoxicillin. Staph infections, including MRSA, occur most frequently among persons in hospitals and healthcare facilities (such as nursing homes and dialysis centers) who have weakened immune systems. MRSA infections that occur in otherwise healthy people who have not been recently (within the past year) hospitalized or had a medical procedure (such as dialysis, surgery, catheters) are known as community-associated (CA)-MRSA infections. These infections are usually skin infections, such as abscesses, boils, and other pus-filled lesions.

MRSA is particularly problematic for a number of reasons. As implied by the name, it is resistant to a number of the strongest antibiotics. Also importantly, MRSA is carried by people who do not exhibit symptoms making it a silent disease. Further, it can be easily transmitted through contact with infected skin or wound tissue. MRSA also causes particularly severe infections in hospitalized patients and persists indefinitely in the skin and noses of persons infected, leaving these people susceptible to subsequent infection.

Although MRSA is the prototypical microorganism responsible for hospital-acquired infection, other organisms are also commonly spread between hospitalized patients by healthcare providers. These include *clostridium difficile*, *enterococcus* species (in particular, vancomycin-resistant *enterococcus* or VRE), *E. coli, pseudomonas aeruginosa*, group A and group B *streptococcus* species, numerous virus species including hepatitis A and B viruses, and other infectious agents.

Despite the obvious societal benefits to reducing the occurrences of nosocomial infections, there are powerful economic incentives as well. For example, Medicare has recently announced that it will no longer reimburse hospitals for certain nosocomial infections. Consequently, a significant portion of the burden of treating such infections will shift to the hospitals, thus providing a further financial motivation to reduce occurrences.

Research has shown that hospital workers are a significant contributor in the transmission of infectious agents to hospitalized patients. For example, certain commonly-used medical instruments are not sanitized sufficiently. One particular instrument that is involved in virtually every patient visit is the stethoscope, but surprisingly, most stethoscopes are cleaned rarely if ever. Collected data has shown that 80% to 100% of stethoscopes used by hospital workers carry infectious agents, including MRSA.

In view of the risks presented by contaminated stethoscopes, certain strategies have been attempted to minimize the transmission of infectious agents, yet none have been satisfactory. One prior art method involves the use of disposable covers that can be placed over the head of the stethoscope. Although proper use can shield a contaminated stethoscope from a patient, the cover reduces the sensitivity of the instrument. Other prior art methods typically involve placing all or a portion of the stethoscope in a cabinet where it can be exposed to a germicidal agent. These methods often suffer from poor compliance due to the length of time and number of steps required to effect the sterilization. Yet another prior art device is a small container holding a sponge saturated with disinfectant. One disadvantage of at least some prior art devices is their portability, which means either they are easily misplaced or they will be located in different areas, reducing the chances their use will become a routine habit. Another disadvantage of at least some prior art devices is that they require two hands to operate (e.g. with a lid that must be unscrewed or otherwise opened) which reduces the ease of use and increases the amount of time required. Yet another disadvantage of at least some prior art devices is that they generally provide no indication of when the amount of disinfectant is exhausted such that they are no longer able to adequately sterilize the stethoscope, leading to a false sense of safety.

BRIEF SUMMARY OF THE INVENTION

The present invention is directed to a sterilizing device for sterilizing at least a portion of a medical instrument. Preferred embodiments of the present invention include a housing, a reservoir suitable for containing sterilizing agent, a delivery system for conducting the sterilizing agent from the reservoir to a permeable membrane, and a lock out system that blocks access to the permeable membrane when insufficient sterilizing agent is present in the reservoir. In preferred embodiments the delivery mechanism is activatable by pressure applied to the permeable membrane by the at least a portion of the medical instrument (e.g. a head of a stethoscope).

In preferred embodiments of the present invention, the delivery system includes a siphon tube, a delivery mechanism, a feed tube, and an activation horn having a series of jets. The siphon tube provides fluid communication between the reservoir and the delivery mechanism. The feed tube provides fluid communication between the delivery mechanism and the series of jets. Activation of the delivery system causes sterilizing agent to be delivered to a substantial portion of the back surface of the permeable membrane.

In preferred embodiments of the present invention, the lock out system includes a balance support system and a lock out mechanism. Reduction of sterilizing agent beyond a certain level causes the balance support system to release the lock out mechanism to block access to the permeable membrane.

The objectives, features, and advantages of the invention will be more readily understood upon consideration of the following detailed description of the invention, taken in conjunction with the accompanying drawing.

BRIEF DESCRIPTION OF THE SEVERAL VIEWS OF THE DRAWINGS

The accompanying drawing which is incorporated in and constitutes a part of this specification, illustrates an exemplary embodiment of the present invention.

DETAILED DESCRIPTION OF THE INVENTION

Figure 1:
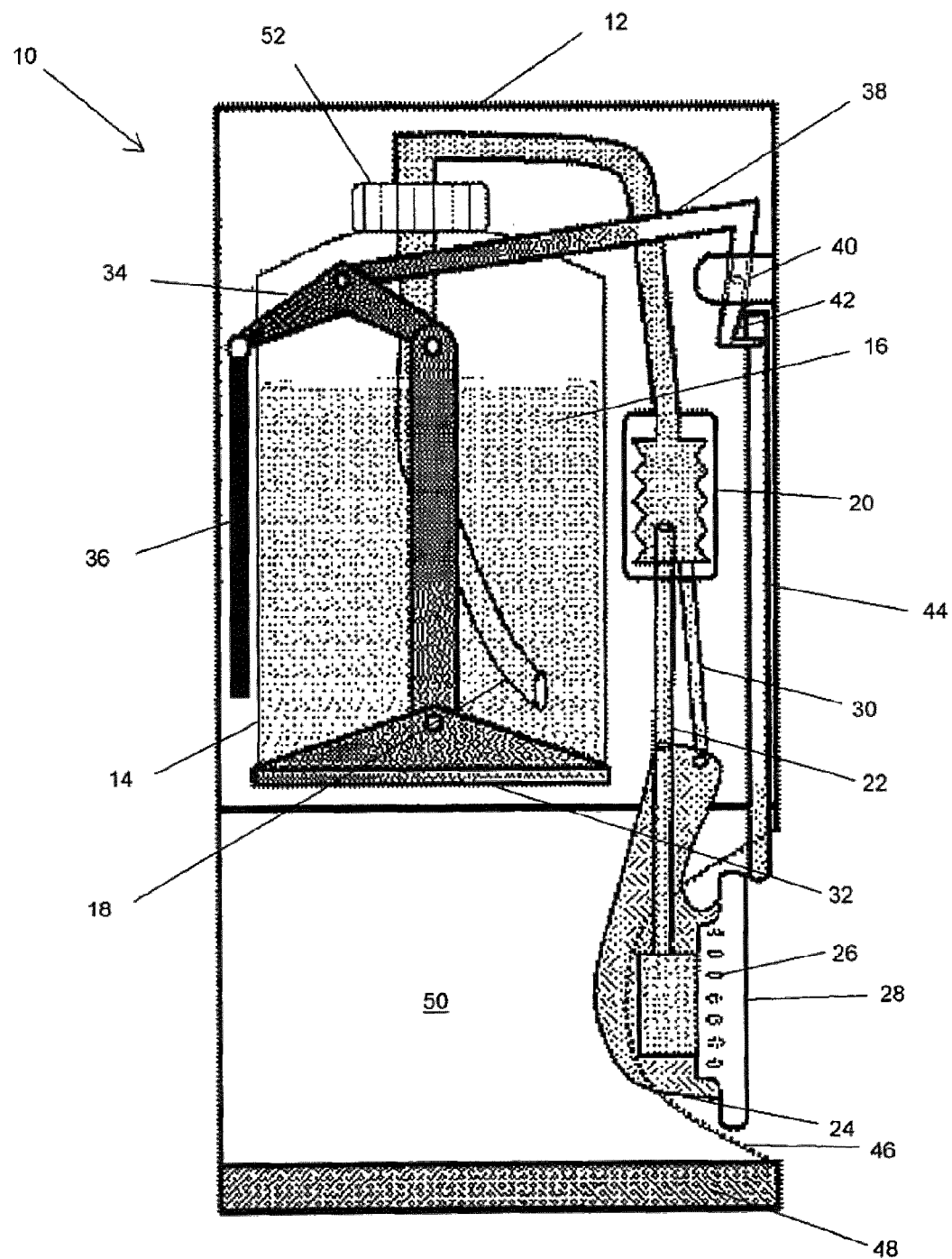
FIG. 1 is a schematic, sectional side view of an exemplary embodiment of the stethoscope sterilizer of the present invention.

The present invention relates generally to devices for cleaning, disinfecting, and/or sterilizing medical instruments in a rapid convenient manner. In a one preferred embodiment, the invention relates to a sterilizing device for instantaneously disinfecting a stethoscope. These devices will be referred to as "sterilizing devices 10" or "sterilizing device systems 10."

In general, preferred embodiments of the sterilizing device systems 10 have a housing 12, a reservoir 14 of sterilizing agent 16, a delivery system (including a delivery mechanism 20 such as a pump) for conducting the sterilizing agent 16 to a site of application such as a permeable membrane 28, and lock out system (including a lock out mechanism such as the lock out door 44) that prevents access to the site of application (e.g. membrane 28) when insufficient sterilizing agent 16 is present in the reservoir 14. The delivery mechanism 20 is preferably activated by pressure applied to the membrane 28 by the portion of the medical instrument to be sterilized (e.g. the head of the stethoscope).

It is an object of some preferred embodiments of the present invention to provide a device 10 for sterilizing a medical instrument in an effective and rapid manner. It is an object of some preferred embodiments of the present invention to provide a relatively simple sterilizing device 10 to facilitate and encourage the sterilizing device's use while ensuring reliability. It is an object of some preferred embodiments of the present invention to provide a fail safe feature to prevent use of the sterilizing device 10 if it is in an inoperable condition. Various embodiments of the present invention may meet one or more of these objects.

Before describing the present invention in detail, it is to be understood that this invention is not limited to particularly exemplified materials, methods, or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents, and patent applications cited herein, whether supra or infra, are hereby incorporated by reference in their entirety.

Finally, as used in this specification and the appended claims, the singular forms "a," "an," and "the" include plural referents unless the content clearly dictates otherwise.

An exemplary embodiment of the present invention such as that shown in FIG. 1 is a system for rapidly and easily disinfecting a medical instrument such as a stethoscope. The sterilizing device system 10 is shown in a schematic, sectional side view and generally includes a main housing 12 adapted to receive a reservoir 14 (shown as a bottle, although not so limited) for holding the sterilizing agent 16. In some preferred embodiments, the housing 12 is configured to be securely mounted to a surface. For example, the housing may include separate or attached mounting elements (e.g. screws or hooks) and/or apertures through which mounting elements may be inserted.

Preferred embodiments of the present invention also include a delivery system for conducting and/or transmitting the sterilizing agent 16 in reservoir 14 to the permeable membrane 28. In the shown exemplary embodiment, the delivery system includes a siphon tube 18, a delivery mechanism 20 (shown as a pump), a feed tube or delivery tube 22 (herein after referred to as feed tube 22), and an activation horn 24 associated with (e.g. covered with or at least positioned substantially adjacent to) a permeable membrane 28. As shown, siphon tube 18 has one end disposed in the reservoir 14 and the other end connects to pump 20 so that siphon tube 18 provides fluid communication between the reservoir 14 and the pump 20. Pump 20 is, in turn, configured to deliver sterilizing agent 16 through the feed tube 22 to the activation horn 24. In the shown embodiment, a mechanical system is used to transmit and/or convert pressure applied to the membrane 28 such that the pump 20 is activated. As shown, a linkage arm 30 connects the activation horn 24 to the pump 20, so that force applied to activation horn 24 is transmitted to the pressurized pump 20. The pump 20, in turn, delivers sterilizing agent 16 through the feed tube 22 to the activation horn 24. In the shown embodiment, a series of jets 26 in fluid communication with the feed tube 22 spray sterilizing agent 16 against the permeable membrane 28, so that a substantial portion of the back surface of the membrane 28 is relatively uniformly coated with sterilizing agent 16.

Preferred embodiments of the present invention also include a lock out system (including a balance support system and a lock out mechanism such as the lock out door 44) that prevents access to the site of application (e.g. membrane 28) when insufficient sterilizing agent 16 is present in the reservoir 14. The shown exemplary embodiment uses a mechanical system that effectively uses the combined weight of the reservoir 14 and sterilizing agent 16 to hold open a sliding lock out door 44. When the combined weight drops (indicating insufficient amounts of sterilizing agent 16), the sliding lock out door 44 is pulled closed by gravity. More specifically, in the shown embodiment the reservoir 14 is supported by a cradle 32, which is in turn carried by one end of a balance arm 34. A counter weight 36 is attached to the other end of the balance arm 34, so that depletion of the sterilizing agent 16 in reservoir 14 will tilt the balance arm 34. A linkage arm 38 is attached at first end to a central point of the balance arm 34 and at a second end to a pivot 40 to a pawl 42. Other known mechanical connectors and supports could be used in place of the linkage arm 38, the pivot 40, and the pawl 42 as would be appreciated by one skilled in the art. The linkage arm 38 transmits the movement of the balance arm 34 through the pivot 40 to the pawl 42. These elements work as a balance support system based on the weight balance of the reservoir 14 and its contents supporting the sliding lock out door 44. The sliding lock out door 44 is restrained against gravity by the pawl 42, so that withdrawal of the pawl 42 releases the lock out door 44 allowing it to slide down and cover the opening 46. This effectively prevents access to the activation horn 24.

In preferred embodiments, the inside bottom (floor) of main housing 12 preferably has a layer of absorbent material 48, such as spun polyethylene terephthalate (e.g. DACRON®), and defines evaporation chamber 50 to manage any excess sterilizing agent that drips from the membrane 28.

In use, an operator places the head of a stethoscope against the permeable membrane 28 of the activation horn 24 and applies pressure (e.g. presses). That force is translated to the pump 20 which delivers sterilizing agent 16 drawn from reservoir 14 by siphon tube 18 through delivery tube 22 to be sprayed against membrane 28 by jets 26. Sterilizing agent 16 wicks through and saturates permeable membrane 28. The pressure and movement of the head of the stethoscope against membrane 28 distributes the sterilizing agent 16 to the head of the stethoscope, killing any infectious agents that may be present. Any excess sterilizing agent 16 drips into evaporation chamber 50 where it is retained by layer of absorbent material 48 until it safely evaporates and disperses. When the amount of sterilizing agent 16 in reservoir 14 falls below a desired level, counter weight 36 deflects balance arm 34. That movement is transferred through linkage arm 38 and pivot 40 to pawl 42. Once pawl 42 is withdrawn a sufficient amount from lock out door 44, gravity causes lock out door 44 to drop across opening 46.

Preferably, the main housing 12 is attached to a stable surface to provide easy access to the activation horn 24. Further, by securing the main housing 12, the operator can activate the sterilization device 10 and sterilize the medical instrument with a simple one-handed operation. Since delivery of the sterilizing agent 16 is directly triggered by pushing the head of the stethoscope against activation horn 24, delivery of the sterilizing agent 16 is essentially instantaneous. As a result, the stethoscope can be disinfected in a very short amount of time, preferably about one second or less.

Membrane 28 is permeable and preferably non-absorbent, allowing the sterilizing agent 16 to wick through from the back surface to the front so that it is transferred to the head of the stethoscope. Also preferably, the front surface of membrane 28 has a texture configured to provide some degree of physical scrubbing to the head of the stethoscope. Further, membrane 28 is preferably non-abrasive to minimize the risk of damage to the diaphragm of the stethoscope or to other delicate features. A presently preferred material is a GORE-TEX® membrane. It should be noted, however, that alternative embodiments of the present invention could include a permeable membrane that is made from a diverse range of materials including, but not limited to terry cloth, cotton, and plastic or wire netting.

In a preferred embodiment, sterilizing agent 16 comprises an alcohol-based agent, such as isopropyl alcohol. This agent is known to be extremely effective against the types of infectious agents likely to be present on stethoscopes and other medical instruments. Further, isopropyl alcohol is commonly used in the hospital and patient care settings, ensuring its ready availability for use in the device. For example, as shown in FIG. 1, lid 52 is removable to allow reservoir 14 to be refilled when the level of sterilizing agent drops. In alternative embodiments, lid 52 could be of a standard size such that the entire reservoir 14 could be replaced. In other embodiments, another suitable germicidal agent or other sterilizing agents may be employed.

In the embodiment shown, the systems have been selected for simplicity and mechanical reliability. Since no electronics are employed, power failure or depleted batteries have no effect on the operation of the sterilizing device system 10. Further, by providing an automatic lock out system, the operator is physically prevented from using the device, ensuring that sterilizing device system 10 will not be used if there is an insufficient amount of sterilizing agent present. This provides a notable advantage over a purely visual or auditory signal in the busy and sometimes chaotic hospital environment.

Nevertheless, one of skill in the art will readily recognize that many of the features can be achieved with alternate mechanisms. In particular, the pump 20, and/or lock out door 44 can be electrically driven, the sterilizing agent level can be determined by a powered sensor, or the activation horn can employ an electric switch, a proximity sensor, or other sensor to determine the presence of the stethoscope and deliver the sterilizing agent 16. In such alternate embodiments, a microprocessor controller (or other suitable electronics) may be used to coordinate the operation of the respective portions of the device.

In yet another embodiment of the device, reservoir 14 can comprise a pressurized supply of sterilizing agent to obviate the need for a separate pump. In these noted embodiments, pressing the stethoscope against activation horn 24 opens a valve, allowing the pressurized sterilizing agent to be delivered to the membrane.

It should be noted that the devices described above have been configured to sterilize a stethoscope. The principles, however, can be applied to any portable medical instrument or other device that may harbor infectious agents. As such, changes and modifications are properly, equitably, and intended to be, within the full range of equivalence of this disclosure.

The terms and expressions that have been employed in the foregoing specification are used as terms of description and not of limitation, and are not intended to exclude equivalents of the features shown and described. This application is intended to cover any adaptations or variations of the present invention. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall therebetween.

What is claimed is:

1. A device for sterilizing at least a portion of a medical instrument, said device comprising:
    (a) a housing;
    (b) a reservoir contained within said housing, said reservoir suitable for containing sterilizing agent;
    (c) a delivery mechanism for conducting said sterilizing agent from said reservoir to a permeable membrane; and
    (d) a lock out mechanism that blocks access to said permeable membrane when insufficient sterilizing agent is present in said reservoir, said lock out system comprising:
        (i) a balance support system; and
        (ii) a lock out mechanism;
        (iii) wherein reduction of sterilizing agent causes said balance support system to release said lock out mechanism to block access to said permeable membrane.

2. The device of claim 1, said delivery mechanism being activatable by pressure applied to said permeable membrane by said at least a portion of said medical instrument.

3. The device of claim 1, said delivery mechanism being activatable by pressure applied to said permeable membrane by a head of a stethoscope.

4. The device of claim 1, said housing configured to be securely mounted to a surface.

5. A device for sterilizing at least a portion of a medical instrument, said device comprising:
    (a) a housing;
    (b) a reservoir suitable for containing sterilizing agent;
    (c) a delivery system for conducting said sterilizing agent from said reservoir to a permeable membrane; and (d) a lock out system that blocks access to said permeable membrane when insufficient sterilizing agent is present in said reservoir, said lock out system comprising:
  (i) a balance support system; and
  (ii) a lock out mechanism;
  (iii) wherein reduction of sterilizing agent causes said balance support system to release said lock out mechanism to block access to said permeable membrane.

6. The device of claim 5, said delivery system including a delivery mechanism activatable by pressure applied to said permeable membrane by said at least a portion of said medical instrument.

7. The device of claim 5, said delivery system including a delivery mechanism activatable by pressure applied to said permeable membrane by a head of a stethoscope.

8. The device of claim 5, said delivery system comprising:
  (a) a siphon tube;
  (b) a delivery mechanism, said siphon tube providing fluid communication between said reservoir and said delivery mechanism;
  (c) a feed tube;
  (d) an activation horn having a series of jets, said feed tube providing fluid communication between said delivery mechanism and said series of jets; and
  (e) said permeable membrane associated with said activation horn;
  (f) wherein activation of said delivery system causes sterilizing agent to be delivered to a substantial portion of the back surface of said permeable membrane.

9. A device for sterilizing at least a portion of a medical instrument, said device comprising:
  (a) a housing;
  (b) a reservoir suitable for containing sterilizing agent;
  (c) a delivery system for conducting said sterilizing agent from said reservoir to a permeable membrane, said delivery system comprising:
    (i) a siphon tube;
    (ii) a delivery mechanism, said siphon tube providing fluid communication between said reservoir and said delivery mechanism;
    (iii) a feed tube;
    (iv) an activation horn having a series of jets, said feed tube providing fluid communication between said delivery mechanism and said series of jets; and
    (v) said permeable membrane associated with said activation horn;
    (vi) wherein activation of said delivery system causes sterilizing agent to be delivered to a substantial portion of the back surface of said permeable membrane; and
  (d) a lock out system that blocks access to said permeable membrane when insufficient sterilizing agent is present in said reservoir, said lock out system comprising:
    (i) a balance support system; and
    (ii) a lock out mechanism;
    (iii) wherein reduction of sterilizing agent causes said balance support system to release said lock out mechanism to block access to said permeable membrane.

10. The device of claim 9, said delivery system including a delivery mechanism activatable by pressure applied to said permeable membrane by said at least a portion of said medical instrument.

11. The device of claim 9, said delivery system including a delivery mechanism activatable by pressure applied to said permeable membrane by a head of a stethoscope.

* * * * *